(12) United States Patent
Creager et al.

(10) Patent No.: US 10,330,532 B2
(45) Date of Patent: Jun. 25, 2019

(54) ELECTRONIC DEVICE WITH A CAMERA AND MOLECULAR DETECTOR

(71) Applicant: HEWLETT-PACKARD DEVELOPMENT COMPANY, L.P., Houston, TX (US)

(72) Inventors: Greg Creager, Boise, ID (US); Lawrence Snyders, Boise, ID (US); Shaun Henry, Boise, ID (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/510,015

(22) PCT Filed: Nov. 10, 2014

(86) PCT No.: PCT/US2014/064756
§ 371 (c)(1),
(2) Date: Mar. 9, 2017

(87) PCT Pub. No.: WO2016/076822
PCT Pub. Date: May 19, 2016

(65) Prior Publication Data
US 2017/0307442 A1    Oct. 26, 2017

(51) Int. Cl.
*G01N 21/00* (2006.01)
*G01J 3/28* (2006.01)
(Continued)

(52) U.S. Cl.
CPC ............... *G01J 3/28* (2013.01); *G01N 33/02* (2013.01); *G06F 17/241* (2013.01);
(Continued)

(58) Field of Classification Search
CPC ... G01J 3/28; G01J 3/51; G01N 21/02; G01N 21/359; G01N 21/65; G01N 15/14;
(Continued)

(56) References Cited

U.S. PATENT DOCUMENTS 7,379,578 B2    5/2008    Soussaline et al.
7,420,663 B2    9/2008    Wang et al.
(Continued)

FOREIGN PATENT DOCUMENTS

CN    101011237 A    8/2007
WO    WO-01/91007 A1    11/2011
(Continued)

OTHER PUBLICATIONS

"Pocket-sized Molecular Sensor to Change How We Interact with the Physical World"; http://www.examiner.com/article/pocket-sized-molecular-sensor-to-change-how-we-interact May 31, 2014; 6 pages.
(Continued)

*Primary Examiner* — Abdullahi Nur
(74) *Attorney, Agent, or Firm* — HPI Patent Department (57) ABSTRACT

Examples of a method to use in an electronic device, an electronic device, and a machine-readable non-transitory storage medium are disclosed herein. An example of the machine-readable non-transitory storage medium includes instructions executable by a processor of an electronic device to generate a molecular signature tag based on molecular signature data representative of a determined molecular structure of an object scanned by a molecular detector of the electronic device and to embed the molecular signature tag in metadata of an image file based on a captured image of the object by a camera of the electronic device.

15 Claims, 11 Drawing Sheets

(51) Int. Cl.
  *G06F 17/24* (2006.01)
  *H04N 5/77* (2006.01)
  *H04N 9/82* (2006.01)
  *H04L 9/32* (2006.01)
  *H04N 5/913* (2006.01)
  *G01N 33/02* (2006.01)
  *G01N 21/359* (2014.01)
  *G01J 3/02* (2006.01)
  *G01J 3/51* (2006.01)

(52) U.S. Cl.
  CPC ............ *H04L 9/3247* (2013.01); *H04N 5/77* (2013.01); *H04N 5/913* (2013.01); *H04N 9/8205* (2013.01); *G01J 3/02* (2013.01); *G01J 3/51* (2013.01); *G01N 21/359* (2013.01); *H04N 2005/91342* (2013.01)

(58) Field of Classification Search
  CPC . G06F 17/02; G06F 17/24; A61B 5/00; A61B 5/0205; A61B 5/026; A61B 5/145; A61B 5/1455
  See application file for complete search history.

(56) References Cited

U.S. PATENT DOCUMENTS

| | | |
|---|---|---|
| 8,392,418 B2 | 3/2013 | Birdwell et al. |
| 8,582,099 B2 | 11/2013 | Guo et al. |
| 2002/0083323 A1 | 6/2002 | Cromer et al. |
| 2006/0241868 A1 | 10/2006 | Sun et al. |
| 2012/0019640 A1 | 1/2012 | Choudury |
| 2012/0249821 A1 | 10/2012 | Imai |
| 2012/0311657 A1 | 12/2012 | Boldyrev et al. |
| 2013/0089248 A1 | 4/2013 | Remiszewski et al. |
| 2015/0065362 A1* | 3/2015 | Gyorffy ............... C12Q 1/6886 506/8 |

FOREIGN PATENT DOCUMENTS

| | | |
|---|---|---|
| WO | WO-2013030850 | 3/2013 |
| WO | WO-2013/052824 A1 | 4/2013 |

OTHER PUBLICATIONS

Roche, P.J.R. et al.; "A Camera Phone Localised Surface Plasmon Biosensing Platform Towards Low-cost Label-free Diagnostic Testing"; Sep. 29, 2011; 8 pages.

* cited by examiner

ELECTRONIC DEVICE WITH A CAMERA AND MOLECULAR DETECTOR

BACKGROUND

End users appreciate performance and features in their electronic devices. They also appreciate ease of use and cost effective solutions for their electronic device needs. Designers and manufacturers may, therefore, endeavor to create and provide electronic devices directed toward at least some of these objectives.

BRIEF DESCRIPTION OF THE DRAWINGS

The following detailed description references the drawings, wherein.

DETAILED DESCRIPTION

An electronic device may include a camera to record images of objects. A user of the electronic device may be interested in determining the molecular composition of the recorded objects. This interest may extend to a variety of different aspects of an object. For example, what is the identity of an object? As another example, is an object fresh or stale? As an additional example, does an object contain contaminants, such as pesticides?

Including a molecular detector in an electronic device having a camera would allow users of such an electronic device both to capture an image of an object and also to determine the molecular composition of this object. Including the determined molecular composition information in the image file of the image of the object captured the camera of the electronic device would allow this molecular composition information to be easily accessed by an end user of the electronic device along with other information relating to the image itself.

Examples directed to addressing technical challenges associated with including a molecular detector in an electronic device having a camera are shown in FIGS. 1-11. These examples allow information relating to the determined molecular composition of an object to be included in the image file of an image of the object captured by a camera of the electronic device.

As used herein, the term "electronic device" represents, but is not necessarily limited to, a tablet, phone, personal digital assistant, imaging device, wearable device, portable computer, or combination thereof. As used herein, the term "image" represents, but is not necessarily limited to, a still image, a single video frame, or multiple video frames. As used herein, the term "camera" represents, but is not necessarily limited to, a device that records images, still and/or video, by utilizing, for example, a lens assembly, shutter, associated electronics, and a photosensitive member or film. Examples of a photosensitive member include, but are not limited to, a charge-coupled device (CCD) or a complementary metal-oxide semiconductor (CMOS).

As used herein, the term "molecular detector" represents, but is not necessarily limited to, a device that includes a light source to illuminate an object with a predetermined wavelength of light (e.g., near infra-red light) and a sensor (e.g., a spectrometer) that analyzes light reflected by the object to determine a molecular composition of the object. As used herein, the term "molecular signature data" represents, but is not limited to, a string of data that represents the molecular composition of an object. The string of data may include, for example, binary digits, alphanumeric characters, or be in any other base numbering system.

As used herein, the term "molecular signature tag" represents, but is not necessarily limited to, a string of data that includes molecular signature data as well as the manufacture identification code, model number and or serial number of the molecular detector. The manufacture identification code, model number and/or serial number of the molecular detector may be concatenated to reduce the size of the molecular signature tag. As used herein, the term "metadata" represents, but is not necessarily limited to, information recorded in an image file of an image of an object. Metadata may be recorded in a predetermined format and structure, such as, for example, the Exchangeable image file format (Exif). Metadata may include, without limitation, information relating to the identification of a camera that captured the image of the object, exposure data for the image, keywords about the image, Global Positioning System (GPS), data regarding the location where an image was captured, timestamp data as to when the image was captured, orientation data of a camera that captured the image and/or biometric data relating to a user of a camera that captured the image.

As used herein, the term "processor" represents, but is not necessarily limited to, an instruction execution system such as a computer-based system, an Application Specific Integrated Circuit (ASIC), a computing device, a hardware and/or machine-readable instruction system, or any combination thereof, that can fetch or obtain the logic from a machine-readable non-transitory storage medium and execute the instructions contained thereon. "Processor" can also include, for example, any controller, state-machine, microprocessor, logic control circuitry, cloud-based utility, service or feature, any other analogue, digital and/or mechanical implementation thereof, or any combination of the forgoing. A processor may be a component of a distributed system.

As used herein, the term "distributed system" represents, but is not necessarily limited to, multiple processors and machine-readable non-transitory storage media in different locations or systems that communicate via a network, such as the cloud. As used herein, the term "cloud" represents, but is not necessarily limited to, computing resources (hardware and/or machine readable instructions) that are delivered as a service over a network (such as the internet). As used her the terms "include", "includes", "including", "have", "has", "having" and variations thereof, mean the same as the terms "comprise", "comprises", and "comprising" or appropriate variations thereof.

As used herein, the term "machine-readable non-transitory storage medium" represents, but is not necessarily limited to, any medium that can contain, store, retain, or maintain programs, code, scripts, information, and/or data. A machine-readable non-transitory storage medium may include any one of many physical media such as, for example, electronic, magnetic, optical, electromagnetic, or semiconductor media. A machine-readable non-transitory storage medium may be a component of a distributed system. More specific examples of suitable machine-readable non-transitory storage media include, but are not limited to, a magnetic computer diskette such as floppy diskettes or hard drives, magnetic tape, a read-only memory (ROM), an erasable programmable read/only memory (EPROM), a flash drive or memory, a compact disc (CD), a digital video disk (DVD), or a memristor.

As used herein, the term "circuitry" represents, but is not necessarily limited to, an interconnection of elements such as, for example, a resistor, inductor, capacitor, voltage source, current source, transistor, diode, application specific integrated circuit (ASIC), gate array, processor, controller, switch, transformer, timer, relay, multiplexor, connector, comparator, amplifier, filter, and/or module having these elements that allow operations to be performed alone or in combination with other elements or components. As used herein, the term "object" represents, but is not necessarily limited to, something material that may be perceived by the senses.

As used herein, the term "coupled" represents, but is not necessarily limited to, any suitable direct and/or indirect connection. For example, if a first component is described as being coupled to a second component, that coupling may be: (1) through a direct electrical and/or mechanical connection, (2) through an indirect electrical and/or mechanical connection via other devices and connections, (3) through an optical electrical connection, (4) through a wireless electrical connection and/or (5) another suitable connection. As used herein, the term "image file" represents, but is not necessarily limited to, digital data in a predetermined format that can be rasterized for use en a display or printer. An image file may store the digital data in an uncompressed, compressed, or vector format. Examples of some predetermined formats for this digital data include, without limitation: Joint Photographic Experts Group (JPEG), Tagged Image File Format (TIFF), raw image data from a camera sensor, and Computer Graphics Metafile (CGM).

Figure 1:
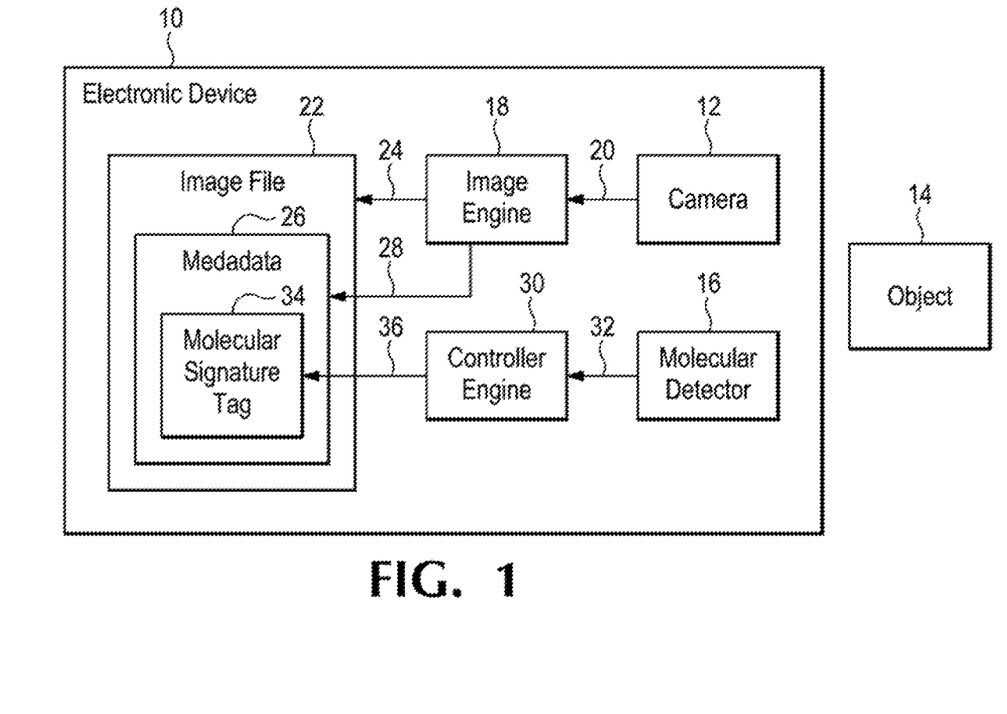
FIG. 1 is an example of an electronic device.

An example of an electronic device 10 is shown in FIG. 1. As can be seen in FIG. 1, electronic device 10 includes a camera 12 to capture an image of an object 14 and a molecular detector 16 to scan object 14 to determine a molecular structure of scanned object 14. As can also be seen in FIG. 1, electronic device 10 additionally includes an image engine 18 coupled to camera 12, as indicated by arrow 20, to generate an image file 22, as indicated by arrow 24, and metadata 26, as indicated by arrow 28, based on the captured image of object 14. Image engine 18 represents any circuitry or combination of circuitry and executable instructions that generates the above-described image file 22 and metadata 26 based on the captured image or object 14. For example, the circuitry may include a processor that executes instructions on a machine-readable non-transitory storage medium to generate the above-described image file 22 and metadata 26 based on the captured image of object 14.

As can additionally be seen in FIG. 1, electronic device 10 includes a controller engine 30 coupled to molecular detector 16, as indicated by arrow 32, to generate a molecular signature tag 34 based on molecular signature data representative of the molecular structure of scanned object 14 received from molecular detector 16 and to et sled molecular signature tag 34 in metadata 26, as indicated by arrow 36. Controller engine 10 represents any circuitry or combination of circuitry and executable instructions that generates the above-described molecular signature tag 34 and embeds molecular signature tag 34 in metadata 26. For example, the circuitry may include a processor that executes instructions on a machine-readable non-transitory storage medium to generate the above-described molecular signature tag 34 and embed molecular signature tag 34 in metadata 26.

Figure 2:
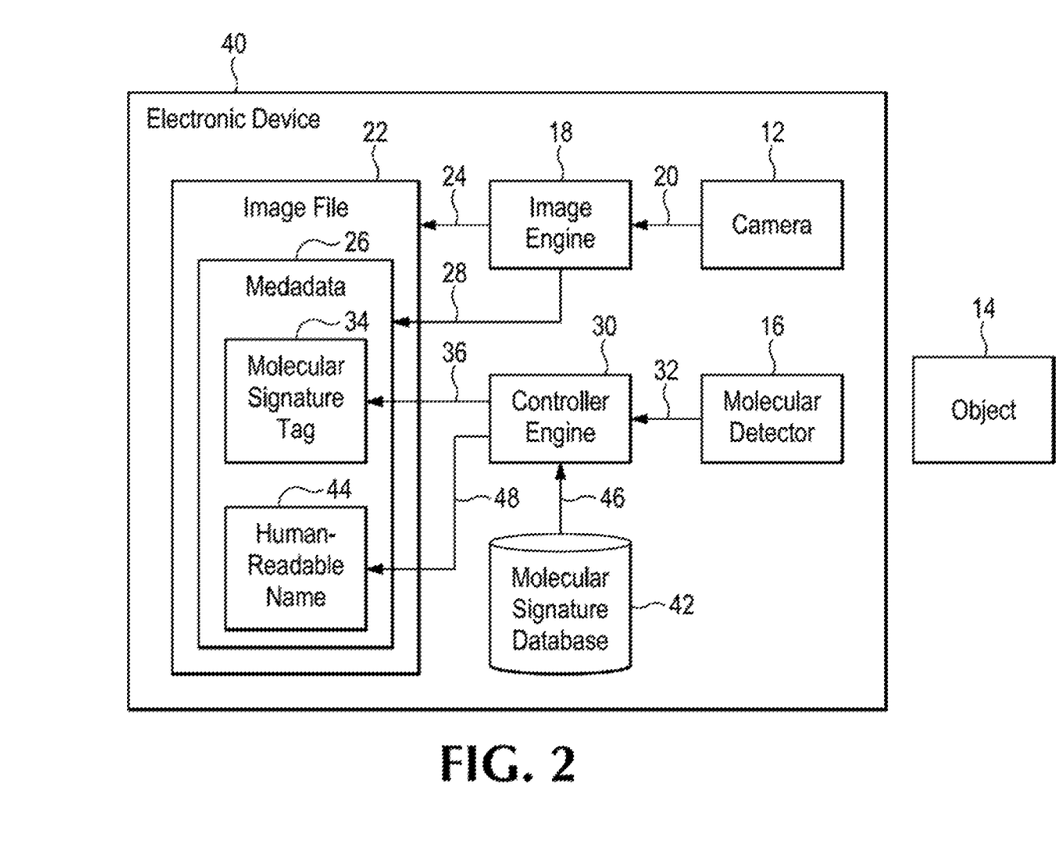
FIG. 2 is another example of an electronic device.

Another example of an electronic device 40 is shown in FIG. 2. Where possible, the same reference numerals have been used for the components and elements of electronic device 40 that are the same as those of electronic device 10. As can be seen in FIG. 2, electronic device 40 includes a molecular signature database 42 of human readable names that relate to molecular structures determined by molecular detector 16. Controller engine 30 is designed to retrieve a particular human-readable name 44 from molecular signature database 42, as indicated by arrow 46, based on the molecular signature data representative of the molecular structure of scanned object 14 received from molecular detector 16. As can also be seen in FIG. 2, controller engine 30 is additionally designed to embed human-readable name 44 in metadata 26, as indicated by arrow 48.

Figure 3:
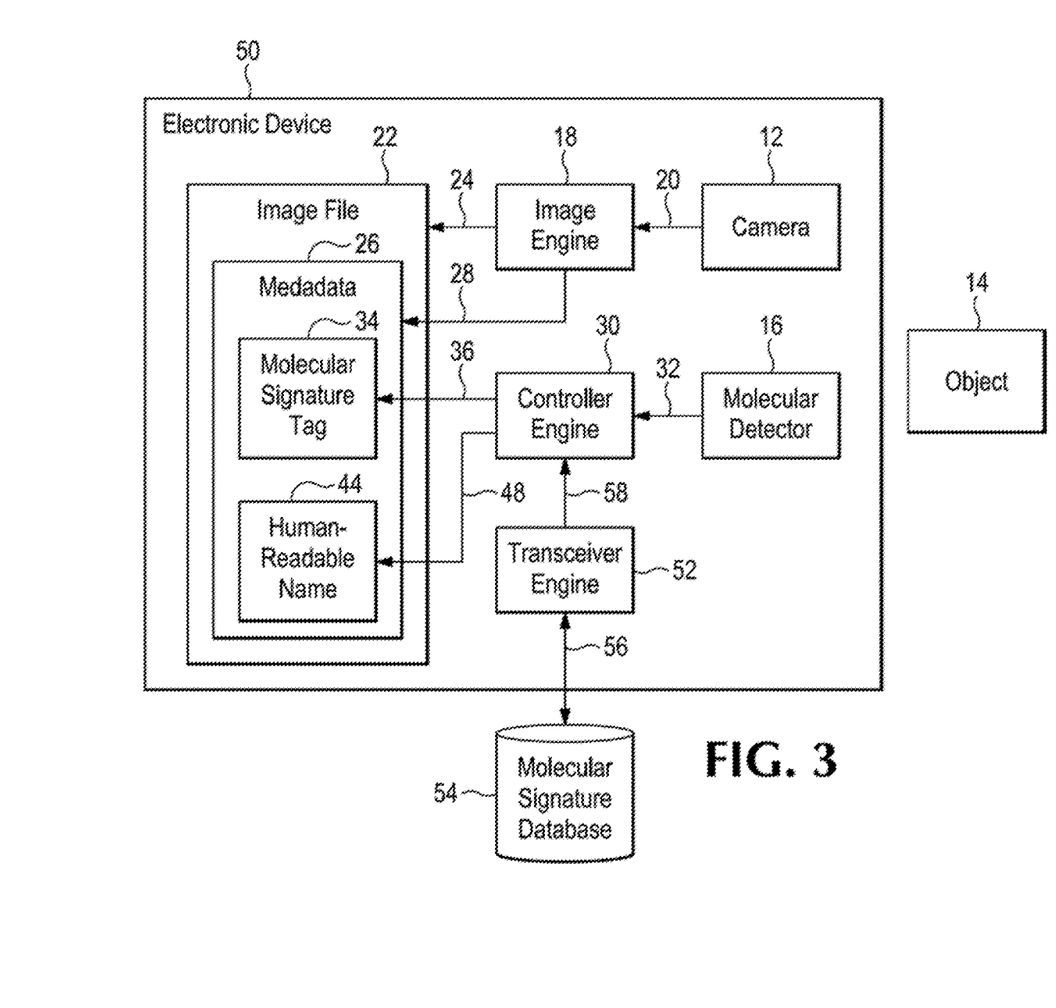
FIG. 3 is an additional example of an electronic device.

An additional example of an electronic device 50 is shown in FIG. 3. Where possible, the same reference numerals have been used for the components and elements of electronic device 50 that are the same as those of electronic device 10. As can be seen in FIG. 3, electronic device 50 includes a transceiver engine 52 to query an external molecular signature database 54 of human-readable names, as indicated by doubled-headed arrow 56, relating both to molecular structures determined by molecular detector 16 and to molecular signature tag 34 generated by controller engine 30. Use of molecular signature tag 34 in connection with the query of external molecular signature database 54 by transceiver engine 52 helps to ensure that molecular signature database 54 is the correct database to query for molecular detector 16. This can be useful for applications where the accuracy and of integrity of human-readable name 44 needs to be assured, such as, for example, forensics and law enforcement.

Transceiver engine 52 also retrieves human-readable name 44 from molecular signature database 54, as also indicated by double-headed arrow 56, based on the molecular signature data from molecular detector 16 that is representative of the molecular structure of scanned object 14. Transceiver engine 52 then transmits human readable name 44 to controller engine 30, as indicated by arrow 58, so that controller engine 30 can embed human-readable name 44 in metadata 26, as indicated by arrow 48. Transceiver engine 52 represents any circuitry or combination of circuitry and executable instructions that performs the above-described query, retrieval, and transmission. For example, the circuitry may include a processor that executes instructions on a machine-readable non-transitory storage medium to perform the above-described query, retrieval, and transmission.

Figure 4:
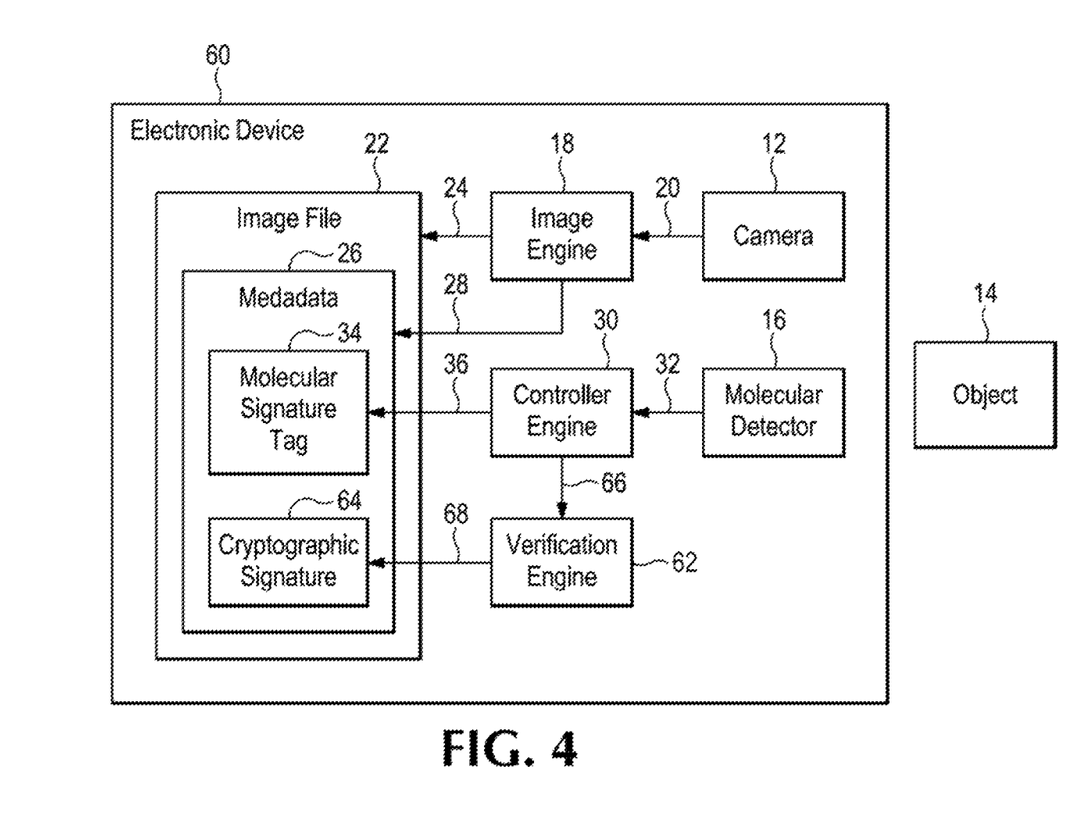
FIG. 4 is a further example of an electronic device.

A further example of an electronic device 60 is shown in FIG. 4. Where possible, the same reference numerals have been used for the components and elements of electronic device 60 that are the same as those of electronic device 10. As can be seen in FIG. 4, electronic device 60 includes a verification engine 62 to generate a cryptographic signature 64 to authenticate that the molecular signature tag generated by controller engine 30, as indicated by arrow 66, is associated with camera 12, molecular detector 16, metadata 26 and/or the content of the captured image (e.g., colorimetric data from the image, a Secure Hash (SH) of the image, a Message Digest (MD) hash of the image, etc.) of object 14. This helps to prevent a counterfeit or modified molecular signature tag from being considered to have been created by electronic device 60.

Verification engine 62 then embeds cryptographic signature 64 within metadata 26, as indicated by arrow 68. Verification engine 62 represents any circuitry or combination of circuitry and executable instructions that generates the above-described cryptographic signature 64 and embeds it in metadata 26. For example, the circuitry may include a processor that executes instructions on a machine-readable non-transitory storage medium to generate the above-described cryptographic signature 64 and embed it in metadata 26.

Figure 5:
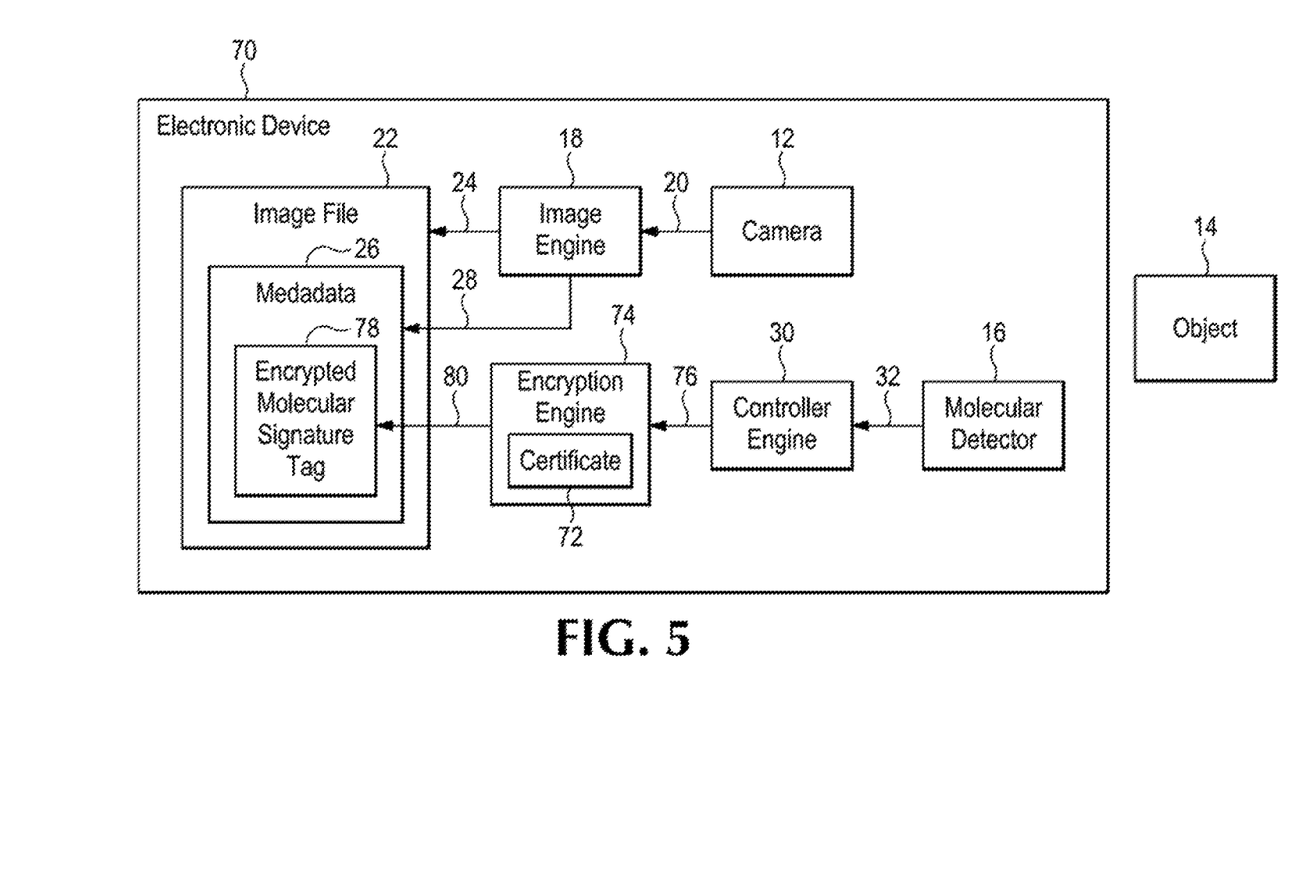
FIG. 5 is an additional further example of an electronic device.

An additional further example of an electronic device 70 is shown in FIG. 5. Where possible, the same reference numerals have been used for the components and elements of electronic device 70 that are the same as those of electronic device 10. As can be seen in FIG. 5, electronic device 70 includes a certificate 72 that has an encryption key which can be installed, for example, by a manufacturer, designer or user of electronic device 70. Electronic device 70 includes an encryption engine 74 to encrypt the molecular signature tag generated by controller engine 30, as indicated by arrow 76, using certificate 72. Encryption engine 74 then embeds encrypted molecular signature tag 78 in metadata 26, as indicated by arrow 80.

This encryption helps to ensure privacy of the content of encrypted molecular signature tag 78. Encryption engine 74 represents any circuitry or combination of circuitry and executable instructions that encrypts the molecular signature tag from controller engine 30 using certificate 72 and embeds encrypted molecular signature tag 78 in metadata 26. For example, the circuitry may include a processor that executes instructions on a machine-readable non-transitory storage medium to encrypt the molecular signature tag from controller engine 30 using certificate 72 and embed encrypted molecular signature tag 78 in metadata 26.

Figure 6:
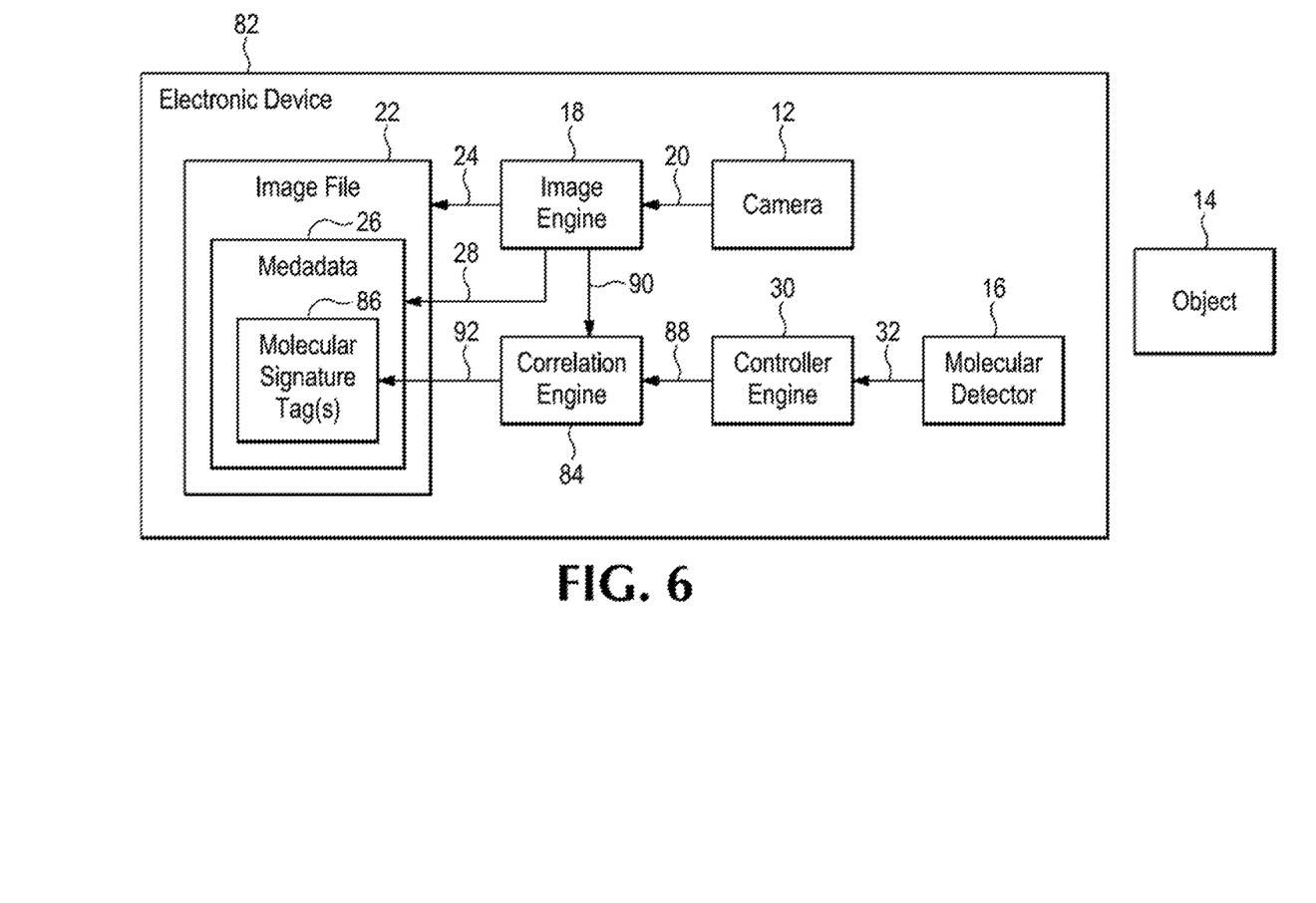
FIG. 6 is yet a further example of an electronic device.

Yet a further example of an electronic device 82 is shown in FIG. 6. Where possible, the same reference numerals have been used for the components and elements of electronic device 82 that are the same as those of electronic device 10. As can be seen in FIG. 6, electronic device 82 includes a correlation engine 84 to associate a molecular signature tag 86 with a region of an image of object 14 captured by camera 12. One way in which this association may be accomplished is for a user of electronic device 82 to pan or move electronic device 82 across object 14. Utilizing this technique, correlation engine 84 operates in conjunction with molecular detector 16 via controller engine 30, as indicated by arrow 88, and image engine 18, as indicated by arrow 90 to record the frames when a particular molecular structure is detected. Correlation engine 84 then utilizes video frame motion detection technology to detect the region of motion of object 14 and to associate a molecular signature tag with that region.

Correlation engine 84 then embeds this molecular signature tag 86 in metadata 26, as indicated by arrow 92. Molecular signature tag 86 includes region information that may be expressed by a particular shape, such as, for example, a pixel "bounding-box" which describes a box of a predetermined number of pixels within an image. This association may be repeated any number of times to associate other molecular signature tags 86 with different regions of the image and/or other molecular signature tags 86 with the same region of the image. Correlation engine 84 represents any circuitry or combination of circuitry and executable instructions that performs the above-described association of molecular signature tag(s) 86 with a region or regions of an image of object 14 captured by camera 12. For example, the circuitry may include a processor that executes instructions on a machine-readable non-transitory storage medium to perform the above-described association of molecular signature tag(s) 86 with a region or regions of an image of object 14 captured by camera 12.

Figure 7:
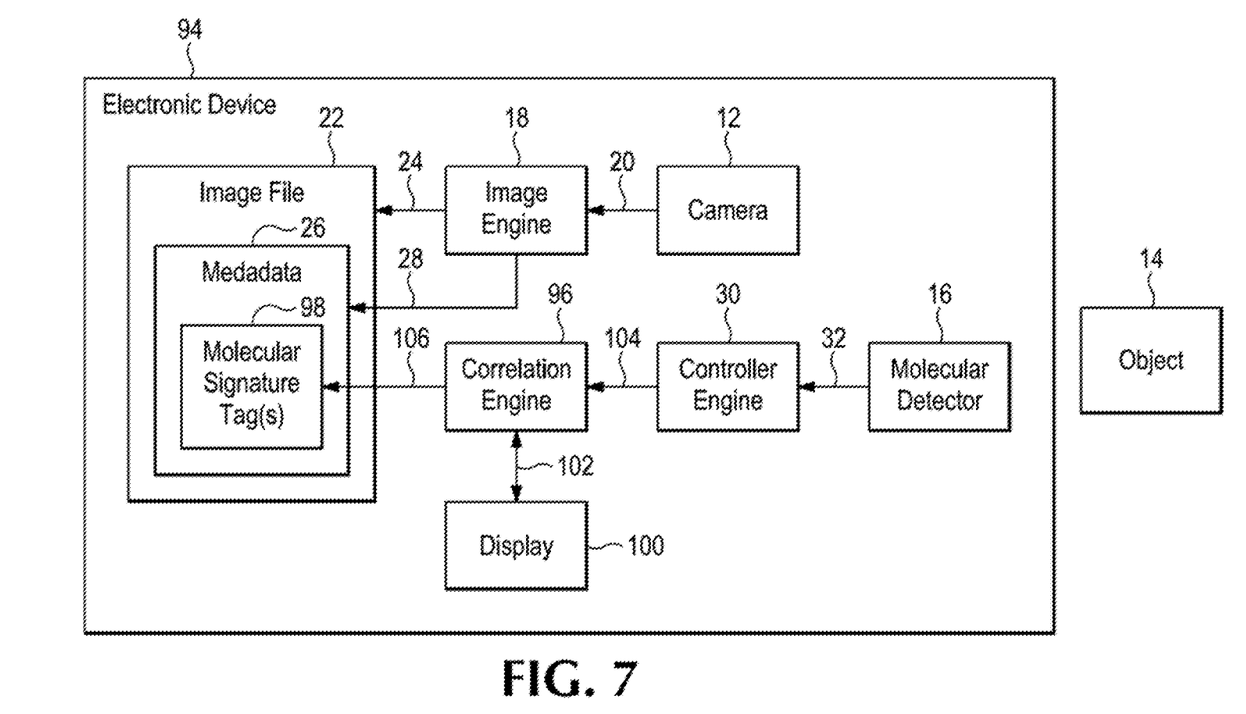
FIG. 7 is a still further example of an electronic device.

A still further example of an electronic device 94 is shown in FIG. 7. Where possible, the same reference numerals have been used for the components and elements of electronic device 94 that are the same as those of electronic device 10. As can be seen in FIG. 7, electronic device 94 includes a correlation engine 96 to associate a molecular signature tag 98 with a region of an image of object 14 captured by camera 12 and a display 100 coupled to correlation engine 96, as indicated by double headed arrow 102. Correlation engine 90 provides a user interface on display 100 to permit a user of electronic device 94 to selectively define the region of the image and to associate the molecular signature tag from controller engine 30, as indicated by arrow 104, with the defined region of the image. This may be accomplished, for example, by selection of a region of the image using a touch-screen user interface on display 100. A list of molecular signatures tags from controller engine 30 may then be presented on display 100 via the user interface on display 100 which the user may select to associate the selected molecular signature tag with the selected region of the image.

Correlation engine 96 then embeds this molecular signature tag 98 in metadata 26, as indicated by arrow 106. This molecular signatures tag 98 includes region information that may be expressed by a particular shape, such as, tar example, a pixel "bounding box" which describes a box of a predetermined number of pixels within an image. This association may be repeated any number of times to associate other molecular signature tags 98 with different regions of the image and/or other molecular signature tags 98 with the same region of the image. Correlation engine 96 represents any circuitry or combination of circuitry and executable instructions that performs the above-described association of molecular signature tag(s) 98 with a region or regions of an image of object 14 captured by camera 12. For example, the circuitry may include a processor that executes instructions on a machine-readable non-transitory storage medium to perform the above-described association of molecular signature tag(s) 98 with a region or regions of an image of object 14 captured by camera 12.

Figure 8:
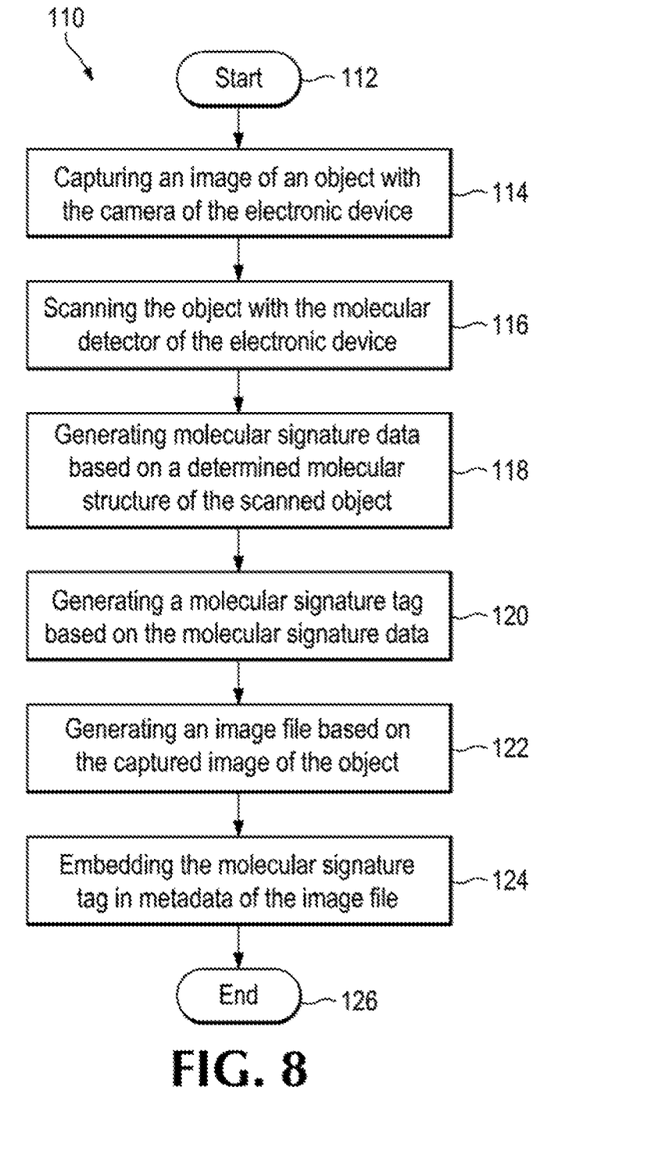
FIG. 8 is an example of a method to use in an electronic device.

An example of a method 110 to use in an electronic device having a camera and a molecular detector is shown in FIG. 8. As can be seen in FIG. 8, method 110 starts 112 by capturing an image of an object with the camera of the electronic device, as indicated by block 114, and scanning the object with the molecular detector of the electronic device, as indicated by block 116. Method 110 continues by generating molecular signature data based on a determined molecular structure of the scanned object, as indicated by block 118, and generating a molecular signature tag based on the molecular signature data, as indicated by block 120. Method 110 additionally continues by generating an image the based on the captured image of the object, as indicated by block 122, and embedding the molecular signature tag in metadata of the image file, as indicated by block 124. Method 110 may then end 126. Method 110 may be used, for example, in electronic device 10 and implemented, for example, partially or completely as described above in connection with electronic device 10.

Figure 9:
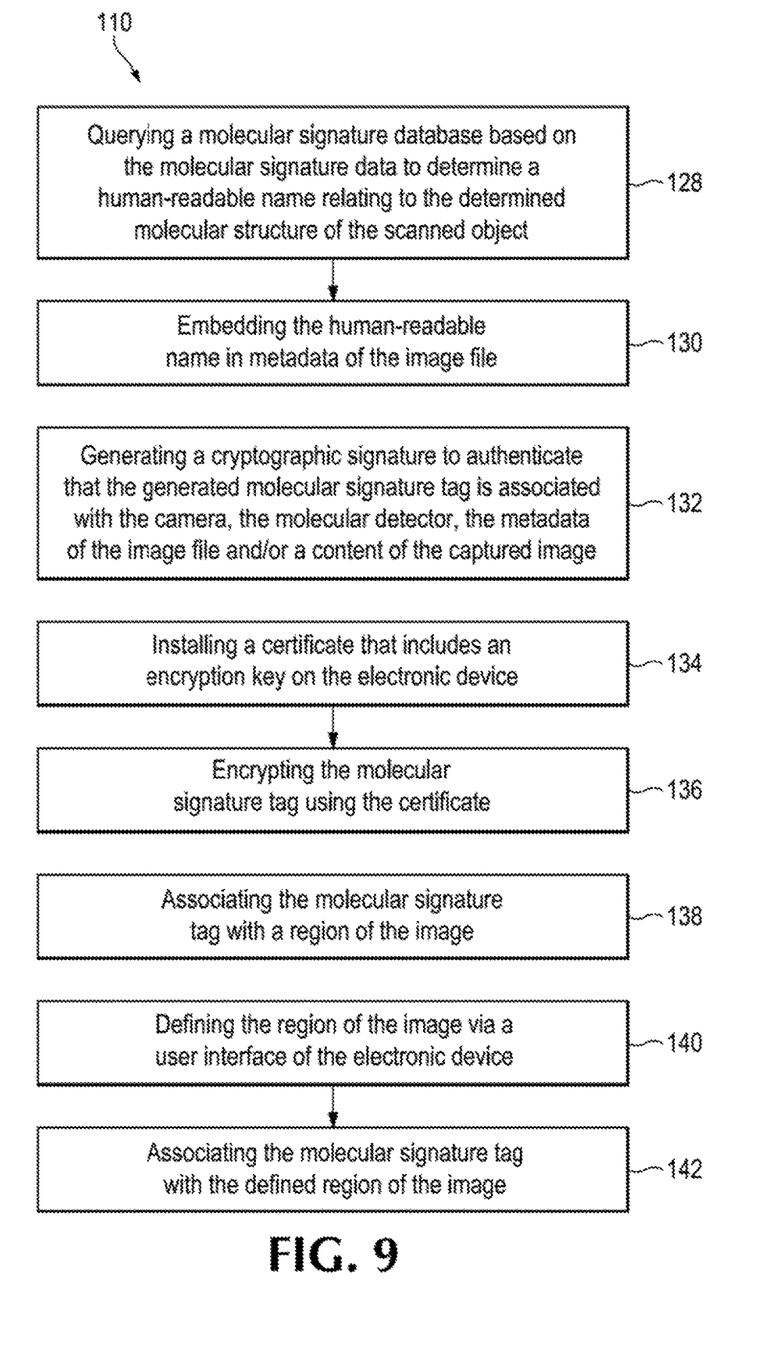
FIG. 9 is an example of additional elements of the method to use in an electronic device of FIG. 8.

An example of additional elements of method 110 is shown in FIG. 9. As can be seen in FIG. 9, method 110 may include querying a molecular signature database based on the molecular signature data to determine a human-readable name relating to the determined molecular structure of the scanned object, as indicated by block 128, and embedding the human-readable name in metadata of the image file, as indicated by block 130. These additional elements 128 and 130 of method 110 may be used, for example, in electronic device 40 and/or electronic device 50 and implemented, for example, partially or completely as described above in connection with electronic device 40 and/or electronic device 50.

As can also be seen in FIG. 9, method 110 may include generating a cryptographic signature to authenticate that the generated molecular signature tag is associated with the camera, the molecular detector, the metadata of the image file and/or a content of the captured image, as indicated by block 132. Additional element 132 of method 110 may be used, for example, in electronic device 60 and implemented, for example, partially or completely as described above in connection with electronic device 60.

As can additionally be seen in FIG. 9, method 110 may include installing a certificate that includes an encryption key on the electronic device, as indicated by block 134, and encrypting the molecular signature tag using the certificate, as indicated by block 136. These additional elements 134 and 136 of method 110 may be used, for example, in electronic device 70 and implemented, for example, partially or completely as described above in connection with electronic device 70.

As can further be seen in FIG. 9, method 110 may include associating the molecular signature tag with a region of the image, as indicated by block 138. Additional element 138 of method 110 may be used, for example, in electronic device 82 and implemented, for example, partially or completely as described above in connection with electronic device 82. Alternatively, associating the molecular signature tag with a region of the image 138 may include defining the region of the image via a user interface of the electronic device, as indicated by block 140, and associating the molecular signature tag with the defined region of the image, as indicated by block 142. In such cases, additional elements 140 and 142 of method 110 may be used, for example, in electronic device 94 and implemented, for example, partially or completely as described above in connection with electronic device 94.

Figure 10:
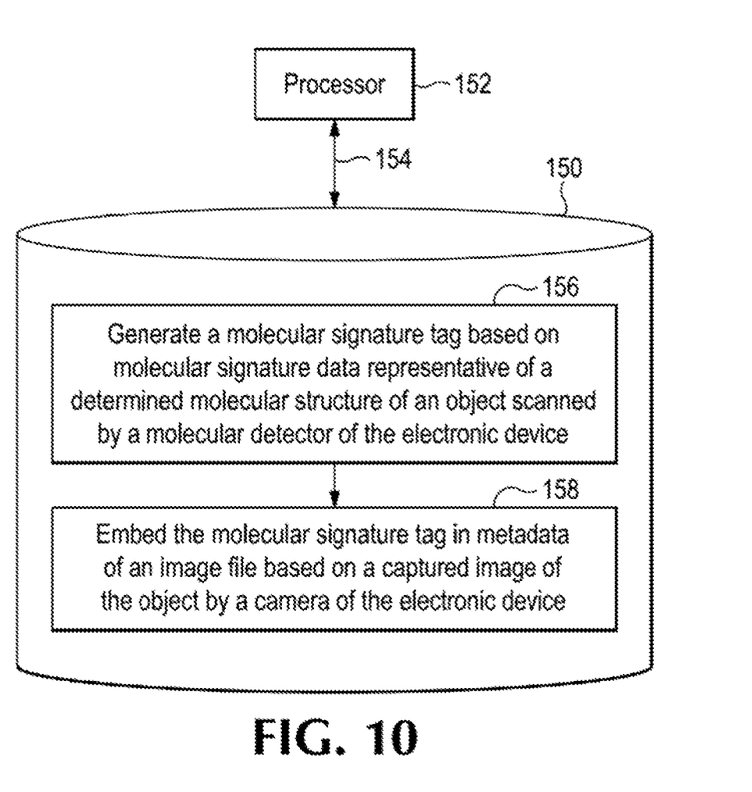
FIG. 10 is an example of machine-readable non-transitory storage medium including instructions executable by a processor of an electronic device.

An example of machine-readable non-transitory storage medium 150 including instructions executable by a processor 152, as indicated by double-headed arrow 154, of an electronic device is shown in FIG. 10. As can be seen in FIG. 10, machine-readable non-transitory storage medium 150 includes instructions 156 executable by a processor 152 of an electronic device to generate a molecular signature tag based on molecular signature data representative of a determined molecular structure of an object scanned by a molecular detector of the electronic device. As can also be seen in FIG. 10, machine-readable non-transitory storage medium 150 includes additional instructions 158 to embed the molecular signature tag in metadata of an image file based on a captured image of the object by a camera of the electronic device. Processor 152 may, for example, be part of electronic device 10. Alternatively or additionally, instructions 156 and/or 158 may be implemented, for example, utilizing at least some of the considerations discussed above in connection with electronic device 10.

Figure 11:
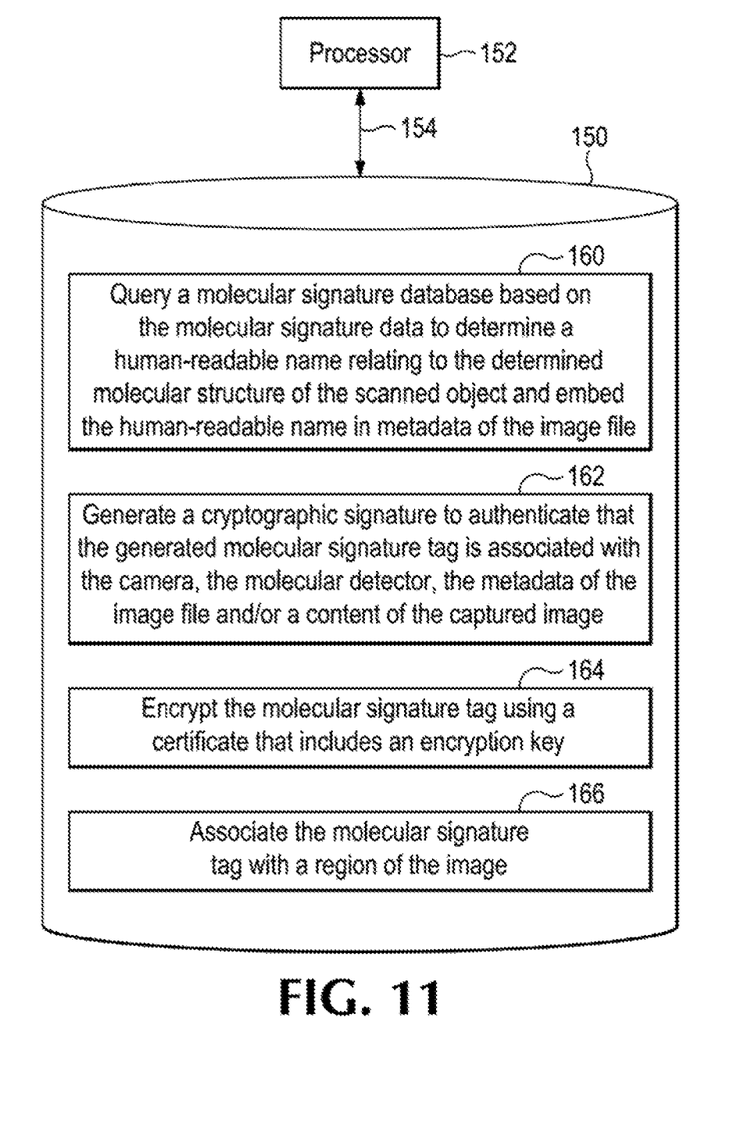
FIG. 11 is an example of additional instructions on the machine-readable non-transitory storage medium of FIG. 10 that are executable by a processor of an electronic device.

An example of additional instructions on machine-readable non-transitory storage medium 150 that are executable by processor 152, as indicated by double-headed arrow 154, of an electronic device are shown in FIG. 11. As can be seen in FIG. 11, machine-readable non-transitory storage medium 150 may include instructions executable by a processor 152 of an electronic device to query a molecular signature database based on the molecular signature data to determine a human-readable name relating to the determined molecular structure of the scanned object and embed the human-readable name in metadata of the image file. In such cases, processor 152 may, for example, be part of electronic device 40 and/or electronic device 50. Alternatively or additionally, instructions 160 may be implemented, for example, utilizing at least some of the considerations discussed above in connection with electronic device 40 and/or electronic device 50.

As can also be seen in FIG. 11, machine-readable non-transitory storage medium 150 may alternatively include instructions 162 executable by a processor 152 of an electronic device to generate a cryptographic signature to authenticate that the generated molecular signature tag is associated with the camera, the molecular detector, the metadata of the image file and/or a content of the captured image. In such cases, processor 152 may, for example, be part of electronic device 60. Alternatively or additionally, instructions 162 may be implemented, for example, utilizing at least some of the considerations discussed above in connection with electronic device 60.

As can additionally be seen in FIG. 11, machine-readable non-transitory storage medium 150 may alternatively include instructions 164 executable by a processor 152 of an electronic device to encrypt the molecular signature tag using a certificate that includes an encryption key. In such cases, processor 152 may, for example, be part of electronic device 70. Alternatively or additionally, instructions 164 may be implemented, for example, utilizing at least some of the considerations discussed above in connection with electronic device 70.

As can additionally be seen in FIG. 11, machine-readable non-transitory storage medium 150 may alternatively include instructions 166 executable by a processor 152 of an electronic device to associate the molecular signature tag with a region of the image. In such cases, processor 152 may, for example, be part of electronic device 82 or electronic device 94. Alternatively or additionally, instructions 166 may be implemented, for example, utilizing at least some of the considerations discussed above in connection with electronic device 82 or 94.

Although several drawings have been described and illustrated in detail, it is to be understood that the same are intended by way of illustration and example. These examples are not intended to be exhaustive or to be limited to the precise form disclosed. Modifications and variations may well be apparent. For instance, other examples of an electronic device, a method to use in an electronic device and/or a machine-readable non-transitory storage medium may include a different combination of components, elements and/or instructions than illustrated and described above. For instance, another example of an electronic device may include both a verification engine and a correlation engine.

Additionally, reference to an element in the singular is not intended to mean one, unless explicitly so stated. Furthermore, method elements are not limited to the sequence or order described and illustrated. Moreover, no element or component is intended to be dedicated to the public regardless of whether the element or component is explicitly recited in the following claims.

What is claimed is:

1. An electronic device having a camera and a molecular detector, the electronic device to:
   capture an image of an object with the camera of the electronic device;
   scan the object with the molecular detector of the electronic device;
   generate molecular signature data based on a determined molecular structure of the scanned object;
   generate a molecular signature tag based on the molecular signature data;
   generate an image file based on the captured image of the object; and
   embed the molecular signature tag in metadata of the image file.

2. The electronic device of claim 1, the electronic device to further:
   query a molecular signature database based on the molecular signature data to determine a human-readable name relating to the determined molecular structure of the scanned object; and
   embed the human-readable name in metadata of the image file.

3. The electronic device of claim 1, the electronic device to further:
   generate a cryptographic signature to authenticate that the generated molecular signature tag is associated with one of the camera, the molecular detector, a content of the captured image, and the metadata of the image file.

4. The electronic device of claim 1, the electronic device to further:
   install a certificate that includes an encryption key on the electronic device; and
   encrypt the molecular signature tag using the certificate.

5. The electronic device of claim 1, the electronic device to further:
   associate the molecular signature tag with a region of the image.

6. The electronic device of claim 5, wherein associating the molecular signature tag with a region of the image comprises:
   defining the region of the image via a user interface of the electronic device; and
   associating the molecular signature tag with the defined region of the image.

7. An electronic device, comprising:
   a camera to capture an image of an object;
   a molecular detector to scan the object to determine a molecular structure of the scanned object;
   an image engine to generate an image file and metadata based on the captured image of the object; and
   a controller engine to generate a molecular signature tag based on molecular signature data representative of the molecular structure of the scanned object and to embed the molecular signature tag in the metadata.

8. The electronic device of claim 7, further comprising:
   a molecular signature database of human-readable names relating to determined molecular structures;
   wherein the controller engine retrieves a particular human-readable name from the molecular signature database based on the molecular signature data representative of the molecular structure of the scanned object; and
   further wherein the controller engine embeds the particular human-readable name in the metadata.

9. The electronic device of claim 7, further comprising:
   a transceiver engine to query a molecular signature database of human-readable names relating both to determined molecular structures and to the molecular signature tag, and to retrieve a particular human-readable name from the molecular signature database based on the molecular signature data representative of the molecular structure of the scanned object; and
   wherein the controller engine embeds the particular human-readable name in the metadata.

10. The electronic device of claim 7, further comprising a verification engine to generate a cryptographic signature to authenticate that the generated molecular signature tag is associated with one of the camera, the molecular detector, a content of the captured image, and the metadata of the image file.

11. The electronic device of claim 7, further comprising:
    a certificate that includes an encryption key; and
    an encryption engine to encrypt the molecular signature tag using the certificate.

12. The electronic device of claim 7, further comprising a correlation engine to associate the molecular signature tag with a region of the image.

13. The electronic device of claim 12, further comprising:
    a display; and
    wherein the correlation engine provides a user interface on the display to permit a user to selectively define the region of the image and to associate the molecular signature tag with the defined region of the image.

14. A machine-readable non-transitory storage medium comprising instructions executable by a processor of an electronic device to:
    generate a molecular signature tag based on molecular signature data representative of a determined molecular structure of an object scanned by a molecular detector of the electronic device; and
    embed the molecular signature tag in metadata of an image file based on a captured image of the object by a camera of the electronic device.

15. The machine-readable non-transitory storage medium of claim 14, further comprising additional instructions executable by the processor of the electronic device to one of:
    query a molecular signature database based on the molecular signature data to determine a human-readable name relating to the determined molecular structure of the scanned object and embed the human-readable name in metadata of the image file;
    generate a cryptographic signature to authenticate that the generated molecular signature tag is associated with one of the camera, the molecular detector, a content of the captured image, and the metadata of the image file;
    encrypt the molecular signature tag using a certificate that includes an encryption key; and
    associate the molecular signature tag with a region of the image.

* * * * *

UNITED STATES PATENT AND TRADEMARK OFFICE
CERTIFICATE OF CORRECTION

PATENT NO. : 10,330,532 B2
APPLICATION NO. : 15/510015
DATED : June 25, 2019
INVENTOR(S) : Greg Creager et al.

It is certified that error appears in the above-identified patent and that said Letters Patent is hereby corrected as shown below:

In the Drawings

In sheet 1 of 11, FIG. 1, reference numeral 26, Line 1, delete "Medadata" and insert -- Metadata --, therefor.

In sheet 2 of 11, FIG. 2, reference numeral 26, Line 1, delete "Medadata" and insert -- Metadata --, therefor.

In sheet 3 of 11, FIG. 3, reference numeral 26, Line 1, delete "Medadata" and insert -- Metadata --, therefor.

In sheet 4 of 11, FIG. 4, reference numeral 26, Line 1, delete "Medadata" and insert -- Metadata --, therefor.

In sheet 5 of 11, FIG. 5, reference numeral 26, Line 1, delete "Medadata" and insert -- Metadata --, therefor.

In sheet 6 of 11, FIG. 6, reference numeral 26, Line 1, delete "Medadata" and insert -- Metadata --, therefor.

In sheet 7 of 11, FIG. 7, reference numeral 26, Line 1, delete "Medadata" and insert -- Metadata --, therefor.

In the Claims

In Column 9, Line 56, Claim 7, delete "a" and insert -- the --, therefor.

In Column 10, Line 28, Claim 12, delete "the" and insert -- with --, therefor.

Signed and Sealed this
Tenth Day of September, 2019

Andrei Iancu
*Director of the United States Patent and Trademark Office*